US012788734B2

(12) United States Patent
Abushakra et al.

(10) Patent No.: US 12,788,734 B2
(45) Date of Patent: Nov. 10, 2026

(54) ALZ-801 FOR USE IN TREATING A COVID-19 ASSOCIATED NEUROLOGICAL SYMPTOM

(71) Applicant: Alzheon, Inc., Framingham, MA (US)

(72) Inventors: Susan Abushakra, Framingham, MA (US); John Hey, Framingham, MA (US); Martin Tolar, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 259 days.

(21) Appl. No.: 18/836,048

(22) PCT Filed: Feb. 7, 2023

(86) PCT No.: PCT/US2023/012501
§ 371 (c)(1),
(2) Date: Aug. 6, 2024

(87) PCT Pub. No.: WO2023/150381
PCT Pub. Date: Aug. 10, 2023

(65) Prior Publication Data

US 2025/0127734 A1 Apr. 24, 2025

Related U.S. Application Data

(60) Provisional application No. 63/412,106, filed on Sep. 30, 2022, provisional application No. 63/407,816, filed on Sep. 19, 2022, provisional application No. 63/307,585, filed on Feb. 7, 2022.

(51) Int. Cl.
*A61K 31/185* (2006.01)
*A61P 25/28* (2006.01)

(52) U.S. Cl.
CPC ............ *A61K 31/185* (2013.01); *A61P 25/28* (2018.01)

(58) Field of Classification Search
None
See application file for complete search history.

(56) References Cited

FOREIGN PATENT DOCUMENTS

| | | |
|---|---|---|
| WO | 2017/044840 A1 | 3/2017 |
| WO | 2020/098492 A1 | 5/2020 |

OTHER PUBLICATIONS

Hey et al., Clinical Pharmacokinetics and Safety of ALZ-801, a Novel Prodrug of Tramiprosate in Development for the Treatment of Alzheimer's Disease. Clin Pharmacokinet. Mar. 2018;57(3):315-333.
Tian et al., GABAA-Receptor Agonists Limit Pneumonitis and Death in Murine Coronavirus-Infected Mice. Viruses. May 2, 20213; 13(6):966, 12 pages.
Tolar et al., Neurotoxic Soluble Amyloid Oligomers Drive Alzheimer's Pathogenesis and Represent a Clinically Validated Target for Slowing Disease Progression. Int J Mol Sci. Jun. 14, 2021;22(12):6355, 14 pages.
Xu et al., A SAGE study of apolipoprotein E3/3, E3/4 and E4/4 allele-specific gene expression in hippocampus in Alzheimer disease. Mol Cell Neurosci. Nov. 2007;36(3):313-31.
International Search Report and Written Opinion for Application No. PCT/US2023/012501, dated Jun. 2, 2023, 16 pages.
International Preliminary Report on Patentability for Application No. PCT/US2023/012501, dated Aug. 22, 2024, 8 pages.

*Primary Examiner* — Samantha L Shterengarts
(74) *Attorney, Agent, or Firm* — McCarter & English, LLP; Michael J. DeGrazia

(57) ABSTRACT

Provided herein are methods for reducing p-tau, Abeta40, Abeta42, and/or the p-tau/Abeta+2 ratio in subjects using ALZ-801. Also provided are methods of treating conditions associated with elevated levels of p-tau, elevated levels of Abeta40, elevated levels of Abeta42, and/or an elevated p-tau/Abeta42 ratio.

12 Claims, 6 Drawing Sheets

ALZ-801 FOR USE IN TREATING A COVID-19 ASSOCIATED NEUROLOGICAL SYMPTOM

RELATED APPLICATIONS

This application is a U.S. National Stage Application filed under 35 U.S.C. § 371, based on International Application No. PCT/US2023/012501, filed on Feb. 7, 2023, which claims the benefit of priority to U.S. Provisional Application No. 63/307,585, filed Feb. 7, 2022; U.S. Provisional Application No. 63/407,816, filed Sep. 19, 2022; and U.S. Provisional Application No. 63/412,106, filed Sep. 30, 2022. The entire contents of each of the above applications are incorporated herein by reference.

BACKGROUND

Infection with the novel coronavirus SARS-COV-2 which causes severe acute respiratory syndrome, was first identified in late 2019 and called COVID-19. COVID-19 infections reached pandemic status by early 2020, and have since affected approximately 400 million people worldwide, leading to approximately 6 million deaths. In the US alone, symptomatic COVID-19 infections affected an estimated 124 million people, leading to approximately 7.5 million hospitalizations and 1 million deaths.

The underlying mechanisms of CNS dysfunction in COVID-19 have been investigated in brain tissue from autopsy material, and from fluid biomarkers obtained from hospitalized COVID-19 patients. Neuropathological studies of patients who died with COVID-19 have shown evidence of focal amyloid deposits even in young patients (see e.g., Rhodes et al. β-Amyloid Deposits in Young COVID Patients, Preprint online at Lancet 2022), and of inflammasome activation and hyper-phosphorylated tau (see e.g., Reiken et al. Alzheimer's Dement. 2022; 1-11).

A large study in hospitalized patients in the US showed increased plasma levels of p-tau, increase p-tau/Abeta42, increased GFAP and t-tau elevations. See e.g., Frontera et al. Alzheimer's Dement. 2021; 1-12. Similar finding of increased p-tau, p-tau/Abeta42 and t-tau was reported from Spain. See e.g., Matias-Guiu et al. Front. Psychol. 2021; 12:724022. Increased GFAP, a marker of astrocyte activation, is a stress response to increased amyloid levels; and p-tau is a marker of neuronal injury frequently seen in neurodegenerative diseases, such as Alzheimer's disease. These collective data suggest that the stressors of acute systemic inflammation, activated endothelium and complement, hypoxia, and/or hypoxic-ischemic insults induce an increase in Abeta42 production and tau hyperphosphorylation resulting in increased Abeta42 and p-tau levels in brain and CSF.

Therapeutic treatments that can inhibit the production of Abeta42, or inhibit the formation of toxic Abeta oligomers, reduce p-tau levels, and/or lower the p-tau/Abeta42 ratio, should therefore ameliorate neuronal injury, rescue neuronal function and improve the cognitive dysfunction related to COVID-19 associated neurological symptoms.

SUMMARY

It has now been found that ALZ-801, a valine prodrug of tramiprosate, is effective at reducing plasma p-$tau_{181}$ and the p-$tau_{181}$/Abeta42 ratio in subjects with early Alzheimer's disease (AD) having at least one ApoE4 allele. See e.g., FIG. 1 where an 18%, 29%, and 41% reduction in plasma p-$tau_{181}$ was observed at 13 weeks, 26 weeks, and 52 weeks respectively, from treatment with 265 mg ALZ-801 administered twice daily. A similar trend is shown in FIG. 2, where a 21%, 30%, and 31% reduction in plasma p-$tau_{181}$/Abeta42 was observed at 13 weeks, 26 weeks, and 52 weeks respectively. Reductions in plasma Abeta40 and Abeta42 were also observed at week 52. See e.g., FIG. 3 and FIG. 4.

Therefore, in one aspect, provided herein are methods for reducing the levels of p-tau in a subject by administering a therapeutically effective amount of ALZ-801, in particular p-$tau_{181}$, and further in particular the plasma levels of p-$tau_{181}$.

Also provided are methods for reducing the ratio of p-tau/Abeta42 in a subject by administering a therapeutically effective amount of ALZ-801, in particular the ratio of p-$tau_{181}$/Abeta42, and further in particular the ratio of p-$tau_{181}$/Abeta42 in plasma.

Also provided are methods for reducing the levels of Abeta40 in a subject by administering a therapeutically effective amount of ALZ-801, in particular plasma levels of Abeta40.

Also provided are methods for reducing the levels of Abeta42 in a subject by administering a therapeutically effective amount of ALZ-801, in particular plasma levels of Abeta42.

Also provided are methods of treating conditions associated with elevated p-tau levels (e.g., elevated p-$tau_{181}$ levels and/or elevated plasma p-$tau_{181}$ levels), elevated Abeta40 (e.g., elevated plasma Abeta40 levels), elevated Abeta42 (e.g., elevated plasma Abeta42 levels), and/or p-tau/Abeta42 ratio (e.g., p-tau 181/Abeta42 ratio and/or plasma p-tau 181/Abeta42 ratio) by administering a therapeutically effective of ALZ-801. Such conditions include COVID-19 associated neurological symptoms.

DETAILED DESCRIPTION

Figure 1:
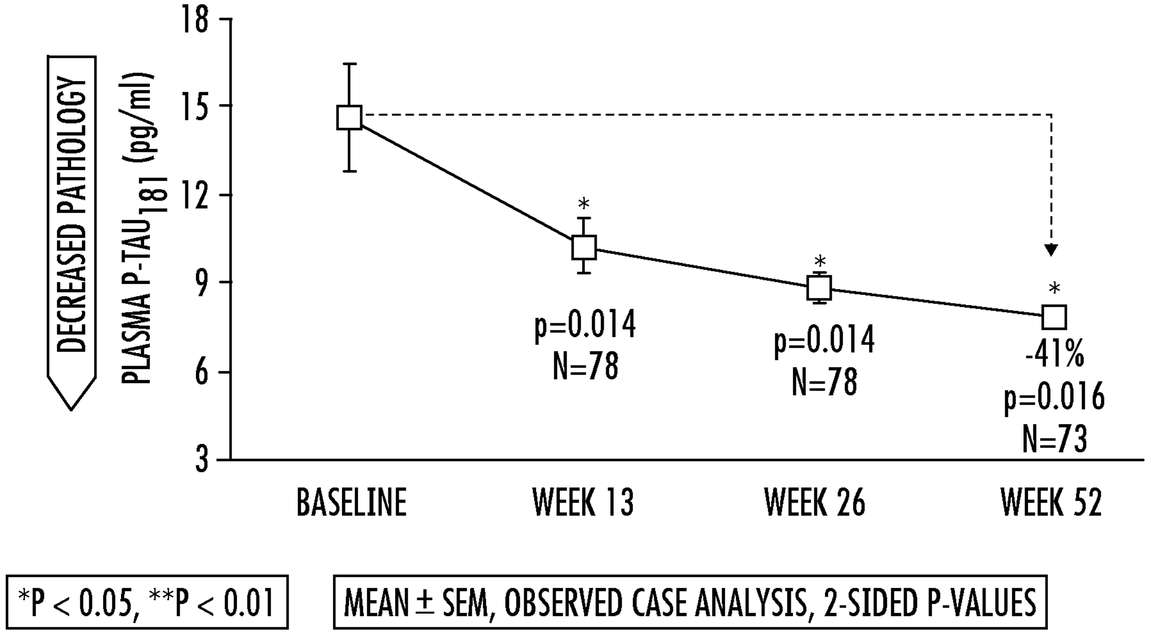
FIG. 1 illustrates the effect on plasma p-$tau_{181}$ following a 52 week treatment with 265 mg ALZ-801 administered orally twice daily to subjects who are $APOE4^+$ and have early AD.

As part of a first embodiment, provided is a method of reducing the levels (e.g., plasma levels) of p-$tau_{181}$ in a subject comprising administering to the subject a therapeutically effective amount of ALZ-801, or a pharmaceutically acceptable salt thereof.

As part of a second embodiment, provided is a method of reducing the p-tau$_{181}$/Abeta42 ratio (e.g., the plasma p-tau$_{181}$/Abeta42 ratio) in a subject comprising administering to the subject a therapeutically effective amount of ALZ-801, or a pharmaceutically acceptable salt thereof.

As part of a third embodiment, provided is a method of reducing the levels (e.g., plasma levels) of Abeta40 in a subject comprising administering to the subject a therapeutically effective amount of ALZ-801, or a pharmaceutically acceptable salt thereof.

As part of a fourth embodiment, provided is a method of reducing the levels (e.g., plasma levels) of Abeta42 in a subject comprising administering to the subject a therapeutically effective amount of ALZ-801, or a pharmaceutically acceptable salt thereof.

ALZ-801 refers to valyl-3-amino-1-propanesulfonic acid (also known as valiltramiprosate), represented by the structure below:

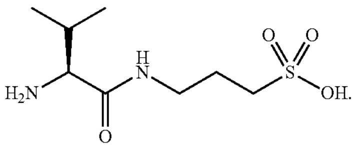

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "effective amount" or "therapeutically effective amount" refers to an amount of ALZ-801 or pharmaceutically acceptable salt that will elicit the recited biological or medical response of a subject e.g., a reduction in p-tau$_{181}$, a reduction in Abeta40, a reduction in Abeta42, a reduction in the p-tau$_{181}$/Abeta42, or to treat a recited condition.

As used herein, the term "treat", "treating" or "treatment" means reversing, alleviating, inhibiting, or slowing the progress of a recited condition or one or more symptoms associated therewith.

As part of a fifth embodiment, provided herein is a method of treating a condition associated with elevated p-tau levels (e.g., elevated plasma p-tau levels), elevated Abeta40 levels (e.g., elevated plasma Abeta 40 levels), elevated Abeta42 levels (e.g., elevated plasma Abeta 42 levels), and/or an elevated p-tau/Abeta42 ratio in a subject comprising administering to the subject a therapeutically effective amount of ALZ-801, or a pharmaceutically acceptable salt thereof. In one aspect of the fifth embodiment, the method decreases p-tau$_{181}$/Abeta42 ratio. In one aspect of the fifth embodiment, the method decreases p-tau$_{181}$/Abeta42 ratio in plasma. In another aspect of the fifth embodiment, the method decreases p-tau$_{181}$ levels. In another aspect of the fifth embodiment, the method decreases p-tau$_{181}$ plasma levels. In another aspect of the fifth embodiment, the method decreases Abeta40 levels. In another aspect of the fifth embodiment, the method decreases plasma Abeta40 levels. In another aspect of the fifth embodiment, the method decreases Abeta42 levels. In another aspect of the fifth embodiment, the method decreases plasma Abeta42 levels.

Conditions associated with elevated p-tau levels, elevated Abeta40 levels, elevated Abeta42 levels, and/or an elevated p-tau/Abeta42 ratio include, but are not limited to, COVID-19 associated neurological symptoms (e.g., encephalopathy such as chronic traumatic encephalopathy, thrombotic strokes, short term memory deficits, cognitive dysfunction such as "Brain Fog", neuropsychiatric disturbances, dizziness, focal symptoms and other neurological symptoms associated with the long-term effects of COVID-19 infection referred to generally as "Long COVID"), traumatic brain injury (acute and/or chronic), single or repetitive brain trauma, mild to severe concussion, hypoxic-ischemic insults post cardiac or cardio-thoracic surgery, post cardiac arrest, and hypertensive vascular dementia. Other conditions include, mild cognitive impairment ("MCI"), vascular dementia, Alzheimer's disease (including early AD, mild to moderate AD, severe AD, and sporadic (non-hereditary) AD), familial (hereditary) age-related cognitive decline, cerebral amyloid angiopathy ("CAA"), hereditary cerebral hemorrhage, senile dementia; Down's syndrome, inclusion body myositis ("IBM"), age-related macular degeneration ("ARMD").

In one aspect, as part of a sixth embodiment, the subject treated herein (e.g., as in any one of the first to fifth embodiments), has AD. Alternatively, as part of a sixth embodiment, the subject treated herein (e.g., as in any one of the first to fifth embodiments), has mild AD. In another alternative, as part of a sixth embodiment, the subject treated herein (e.g., as in any one of the first to fifth embodiments), has mild-to-moderate AD.

In one aspect, as part of a seventh embodiment, the subject treated herein (e.g., as in any one of the first to sixth embodiments), is of the APOE4/4 or APOE3/4 genotype. Alternatively, as part of a seventh embodiment, the subject treated herein (e.g., as in any one of the first to sixth embodiments), is of the APOE3/4 genotype.

In one aspect, as part of an eighth embodiment, the subject treated herein has memory deficiency attributed to any of the foregoing disclosed conditions and demonstrates an improvement in memory after treatment with ALZ-801. In some aspects of the eighth embodiment, the improvement in memory occurs within 26 weeks of treatment. In some aspects of the eighth embodiment, the improvement in memory occurs between about 13 and about 26 weeks of treatment.

In one aspect, as part of a ninth embodiment, the subject treated herein (e.g., as in any one of the first to eighth embodiments), is administered 530 mg ALZ-801/day. Alternatively, as part of a ninth embodiment, the subject treated herein (e.g., as in any one of the first to eighth embodiments), is administered 265 mg ALZ-801 twice daily (BID). In some aspects of the ninth embodiment, the ALZ-801 is administered orally. In some aspects of the ninth embodiment, the ALZ-801 is administered daily at least until an improvement of the disease or condition is observed. In some aspects of the ninth embodiment, the ALZ-801 is continued to be administered daily after an improvement of the disease or condition is observed.

Exemplification

Evaluation of disease modifying effects from phase 2 trial of ALZ-801 (valiltramiprosate) in subjects with early Alzheimer's disease were conducted. The study enrolled 84 patients, with early AD, who carry the APOE4/4 or APOE3/4 genotype and have an MMSE score ranging from 22 to 30 (CDR-G 0.5 or 1). Each patient received 265 mg ALZ-801 twice daily. The average MMSE score of the subjects was 26 (mean age 69 years, 52% female). Subjects were either amyloid PET positive or A+/T+ on CSF assays. CSF criteria were: Ratio of Aβ42/40×10≤0.61, and p-tau181≥61 pg/ml. CSF was evaluated at 52 weeks, and plasma biomarkers at every visit.

All fluid biomarker analyses were performed at the Neurochemistry Laboratory of Dr. Blennow (Molndal, Sweden), and were blinded to subject's demographics or genotype. CSF biomarker assays were analyzed using Lumipulse (Fujirebio) and plasma assays utilized Simoa assays. Cognitive tests include the Rey Auditory Verbal Learning Test (RAVLT: immediate, delayed and recognition memory) and Digit Symbol Substitution Tests (DSST), and a composite Z-score is calculated (3-item RAVLT+DSST). Change from baseline (CBL) analyses were performed on the mITT population and included all observed data, using paired t-tests and 2-sided p-values. The primary biomarker outcome was p-$tau_{181}$.

Figure 2:
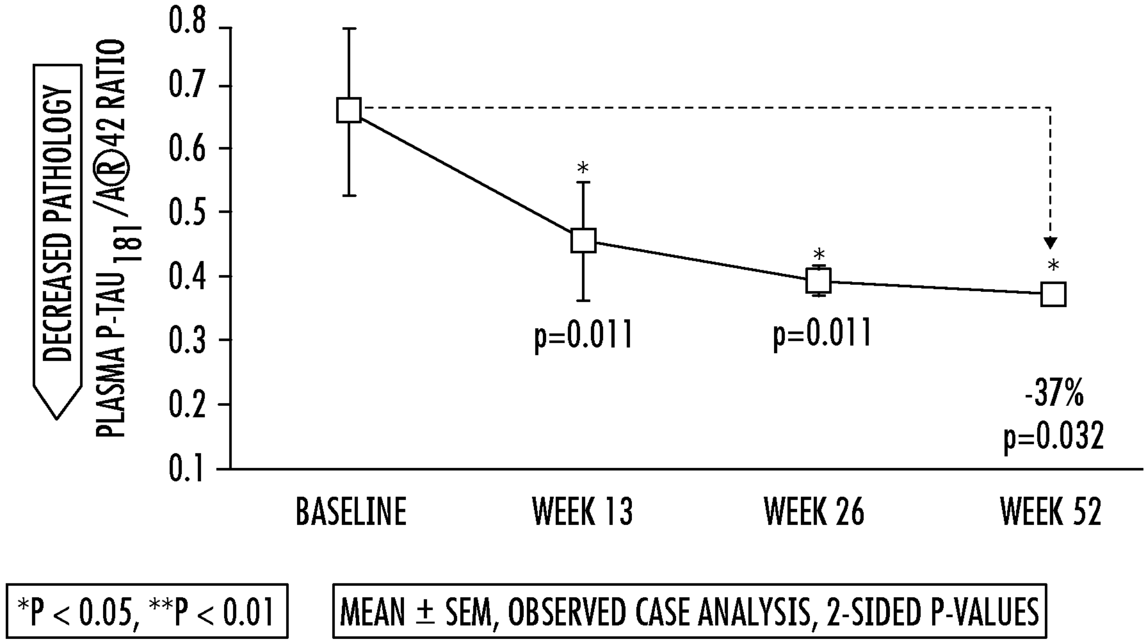
FIG. 2 illustrates the effect on the p-$tau_{181}$/Abeta42 ratio following a 52 week treatment with 265 mg ALZ-801 administered orally twice daily to subjects who are $APOE4^+$ and have early AD.

Of the 84 APOE4 carrier that were enrolled and received ALZ-801, 80 and 75 subjects completed 26 and 52 weeks respectively. In this population, ALZ-801 265 mg BID demonstrated a 41% reduction in plasma p-$tau_{181}$ (p=0.016) at 52 weeks, a 29% reduction in plasma p-$tau_{181}$ (p=0.014) at 26 weeks, and a 18% reduction at 13 weeks (p=0.014). See FIG. 1. ALZ-801 also significantly reduced the plasma p-tau 181/Aβ42 ratio by 37% at 52 weeks (p=0.032), 30% at 26 weeks (p=0.011), and by 21% at 13 weeks (p=0.011). See FIG. 2. This is much greater than the annualized ~12% reduction in plasma p-$tau_{181}$ observed in the recent human clinical trials of the anti-amyloid antibody lecanemab (van Dyck, C H et al., N Engl J Med 2023; 388:9-21, DOI: 10.1056/NEJMoa2212948).

Figure 3:
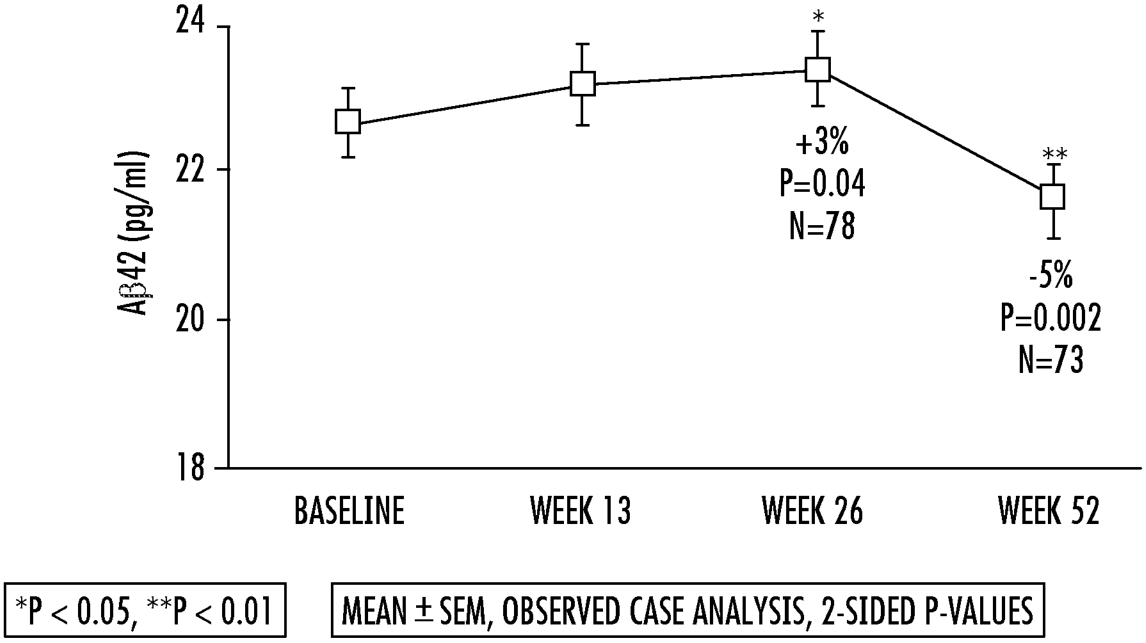
FIG. 3 illustrates the effect on plasma Abeta42 following a 52 week treatment with 265 mg ALZ-801 administered orally twice daily to subjects who are $APOE4^+$ and have early AD.
Figure 4:
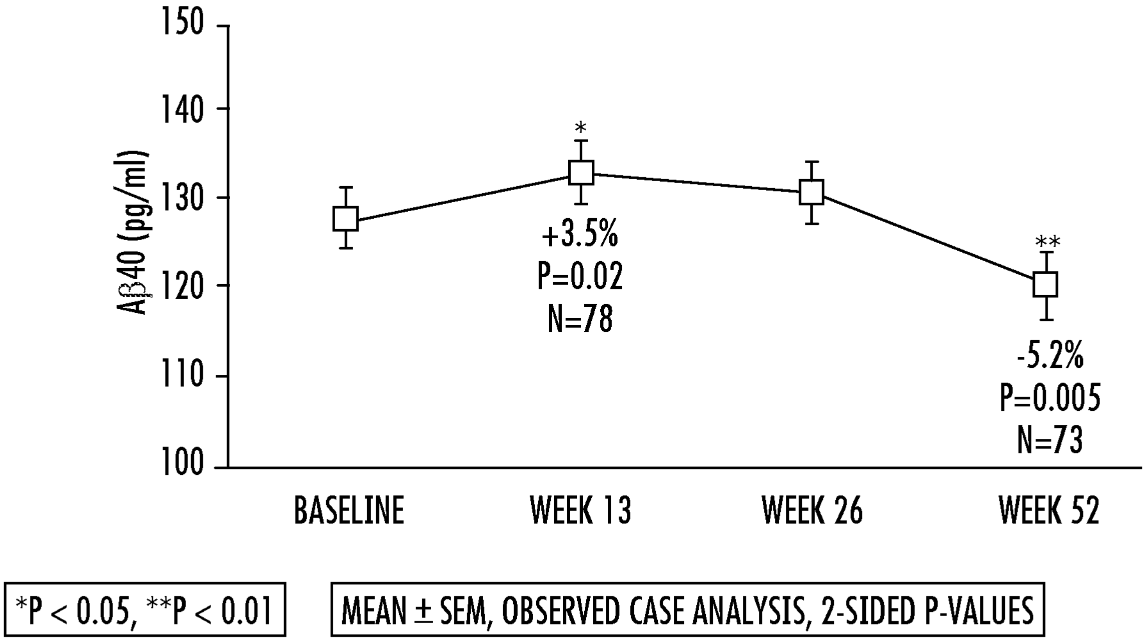
FIG. 4 illustrates the effect on plasma Abeta40 following a 52 week treatment with 265 mg ALZ-801 administered orally twice daily to subjects who are $APOE4^+$ and have early AD.

Target engagement of ALZ-801 was further validated in this population by data showing an increase in the plasma levels of Abeta40 and Abeta42 at 13-26 weeks, followed by significant 5% reductions in each at 52 weeks (p=0.002 and p=0.005, respectively). See FIGS. 3 and 4. Mechanistically, ALZ-801 is believed to inhibit β-amyloid oligomer formation in the brain resulting in the inhibition of both formation of oligomers and subsequent aggregation. Aggregation and fibril formation of amyloid-β Abeta40 and Abeta42 peptides are central events in subjects with early Alzheimer's disease. At baseline, untreated subjects possess a certain level of Abeta40 and Abeta42 in both the brain and plasma. When treated with ALZ-801, however, initial increases in plasma Abeta40 and Abeta42 were observed, supporting the belief that amyloid aggregation in the brain is being blocked, and Abeta40 and Abeta42 are being cleared into the plasma. Sec e.g., the initial surge in plasma Abeta42 and Abeta40 observed in weeks 1-26 and 1-13 of treated subjects as illustrated in FIG. 3 and FIG. 4. Following this, overall reduction in plasma Abeta40 and Abeta42 was then observed, indicating that ALZ-801 had promoted efficient clearance of soluble amyloid beta species from the brain.

Figure 5:
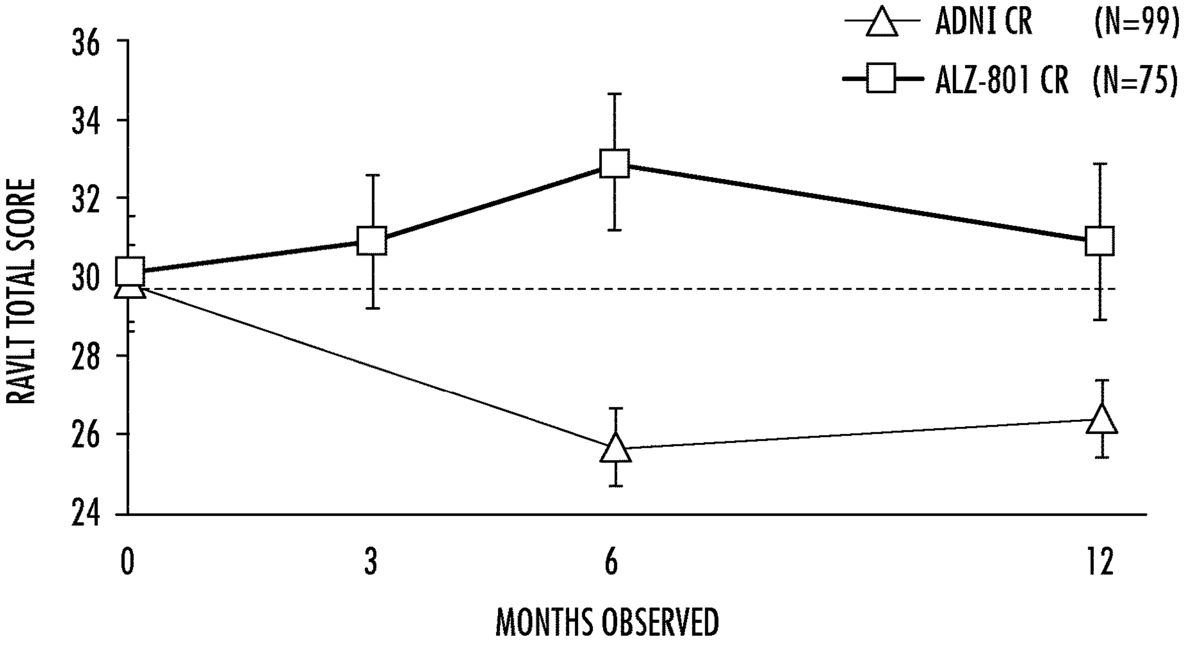
FIG. 5 illustrates the effect on memory as measured by RAVLT following a 52 week treatment with 265 mg ALZ-801 administered orally twice daily to subjects who are $APOE4^+$ and have early AD.

In this study population, ALZ-801 also demonstrated a sustained improvement in memory tests. Clinical outcomes were taken from subjects in the Alzheimer's Disease Neuroimaging Initiative (ADNI). ADNI is a longitudinal database registry of clinical, imaging, and biomarker captured in AD subjects and cognitive normal subjects accepted by the FDA for retrospective research as an external historical control comparator group. Real word evidence (RWE) are data collected on individuals that fall outside of data captured in clinical trials. In this case, we integrated ADNI as a RWE source to serve as an external control arm. As shown by FIG. 5, treatment with ALZ-801 showed memory improvements up to about 6-months and maintained an improvement over baseline using the Rey's Auditory Verbal Learning Test ("RAVLT"). These results were consistently superior to the cognitive results for AD severity- and genotype-matched, untreated patients as obtained from the ADNI database.

Figure 6:
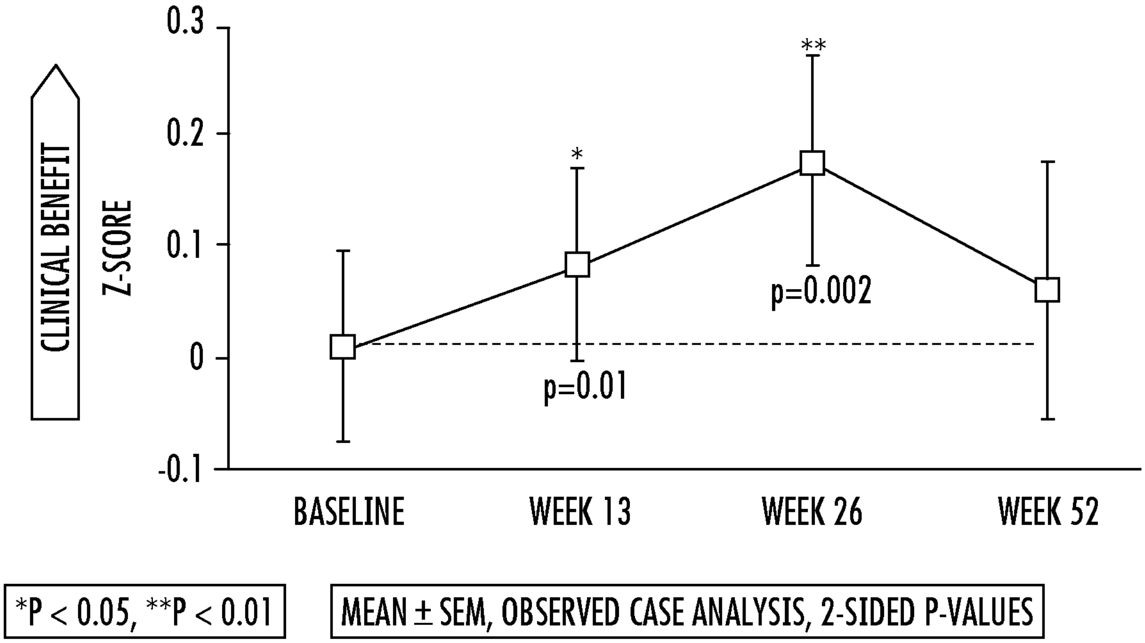
FIG. 6 illustrates the improvement in cognition following a 52 week treatment with 265 mg ALZ-801 administered orally twice daily to subjects who are $APOE4^+$ and have early AD as determined by a composite Z-score based on 3 RAVLT tests and a digit symbol substitution test (DSST).

As shown in FIG. 6, the composite Z-score of cognition of subjects in this clinical trial ((RAVLT memory scores+DSST) showed significant increase at 26 weeks (p=0.002) and remained numerically above baseline after 52 weeks of treatment with ALZ-801.

While certain data presented is specific for p-$tau_{181}$, without being bound by theory, applicants believe other forms of phosphorylated tau protein, e.g., p-$tau_{217}$ and p-$tau_{231}$ will also be reduced by treatment with ALZ-801. Accordingly, the disclosure also provides for the treatment of diseases and conditions associated with abnormally high levels of any of the isoforms of p-tau by the administration of ALZ-801.

In addition, the subjects in this clinical trial, showed an approximate 20% annualized reduction in atrophy of hippocampal volume on ALZ-801 as compared to a well-matched ADNI cohort (p=0.05). This preservation of hippocampal volume showed significant correlations with cognitive benefits (Spearman's 0.27, p=0.02) suggesting neuroprotection. In contrast, Lecanemab did not demonstrate any significant annualized reduction in hippocampal volume atrophy. Van Dyck, 2022, supra.

Unlike anti-amyloid antibodies, such as Lecanemab, ALZ-801 treatment over 52 weeks also appeared to show an ~15% reduction in ventricular volume expansion as measured by MRI (p=0.08).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) that may be cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating a COVID-19 associated neurological symptom in a subject in need thereof, comprising administering to the subject a therapeutically effective amount of ALZ-801, or a pharmaceutically acceptable salt thereof.

2. The method of claim 1, wherein the treatment reduces p-$tau_{181}$ levels in the subject.

3. The method of claim 1, wherein the treatment reduces p-$tau_{181}$/Abeta42 ratio in the subject.

4. The method of claim 1, wherein the treatment reduces Abeta40 levels in the subject.

5. The method of claim 1, wherein the treatment reduces Abeta42 levels in the subject.

6. The method of claim 1, wherein the COVID-19 associated neurological symptom is selected from encephalopathy, thrombotic stroke, short term memory deficit, cognitive dysfunction, neuropsychiatric disturbance, dizziness, focal symptom, traumatic brain injury, single or repetitive trauma, mild to severe concussion, hypoxic-ischemic insults post cardiac or cardio-thoracic surgery, post cardiac arrest, and hypertensive vascular dementia.

7. The method of claim 1, wherein the p-tau$_{181}$ levels, the Abeta40 levels, the Abeta42 levels, and the p-tau$_{181}$/Abeta42 ratio refer to the levels and ratio in plasma.

8. The method of claim 1, wherein the subject is administered 530 mg ALZ-801/day.

9. The method of claim 8, wherein the subject is administered 265 mg ALZ-801 twice daily.

10. The method of claim 1, wherein the subject also is suffering from mild AD.

11. The method of claim 1, wherein the subject is of the APOE4/4 or APOE3/4 genotype.

12. The method of claim 11, wherein the subject is of the APOE3/4 genotype.

* * * * *